US012656354B2

(12) United States Patent
Kojima et al.

(10) Patent No.: US 12,656,354 B2
(45) Date of Patent: Jun. 16, 2026

(54) OXYTOCIN PURIFYING METHOD AND MEASURING METHOD AND KIT

(71) Applicant: FUJIFILM Wako Pure Chemical Corporation, Osaka (JP)

(72) Inventors: Masaaki Kojima, Shibukawa (JP); Fumie Akutsu, Shibukawa (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 502 days.

(21) Appl. No.: 18/278,756

(22) PCT Filed: Feb. 24, 2022

(86) PCT No.: PCT/JP2022/007718
§ 371 (c)(1),
(2) Date: Aug. 24, 2023

(87) PCT Pub. No.: WO2022/181717
PCT Pub. Date: Sep. 1, 2022

(65) Prior Publication Data
US 2024/0133901 A1      Apr. 25, 2024
US 2024/0230684 A9      Jul. 11, 2024

(30) Foreign Application Priority Data

Feb. 26, 2021     (JP) ................................. 2021-031161

(51) Int. Cl.
*G01N 33/74*          (2006.01)
*G01N 1/34*           (2006.01)

(52) U.S. Cl.
CPC ............... *G01N 33/74* (2013.01); *G01N 1/34* (2013.01); *G01N 2410/04* (2013.01)

(58) Field of Classification Search
CPC ...... G01N 1/34; G01N 2410/04; G01N 33/68; G01N 33/74; C07K 7/16
See application file for complete search history.

(56) References Cited

U.S. PATENT DOCUMENTS

| | | | |
|---|---|---|---|
| 6,998,470 | B1 | 2/2006 | Gallagher et al. |
| 2020/0140482 | A1 | 5/2020 | Nitta |

FOREIGN PATENT DOCUMENTS

| | | |
|---|---|---|
| CN | 108445116 A | 8/2018 |
| CN | 110016072 A | 7/2019 |
| JP | 2019-148554 A | 9/2019 |
| WO | WO 2016/140063 A1 | 9/2016 |
| WO | WO 2018/221745 A1 | 12/2018 |

OTHER PUBLICATIONS

Extended European Search Report for corresponding European Application No. 22759752.3, dated Jul. 22, 2024.

Franke et al., "Oxytocin analysis from human serum, urine, and saliva by orbitrap liquid chromatography-mass spectrometry," Drug Testing and Analysis, vol. 11, 2019, pp. 119-128.

Vickers et al., "Hydrolysis of Biological Peptides by Human Angiotensin-converting Enzyme-related Carboxypeptidase," Journal of Biological Chemistry, vol. 277, No. 17, 2002, pp. 14838-14843.

Zhang et al., "Ultra sensitive quantitation of endogenous oxytocin in rat and human plasma using a two-dimensional liquid chromatography-tandem mass spectrometry assay," Analytical Biochemistry, vol. 416, 2011, pp. 45-52.

Higuchi et al., "Functional development of the oxytocin release mechanism and its role in the initiation of parturition in the rat," Journal of Endocrinology, vol. 106, 1985, pp. 311-316.

Japanese Office Action for corresponding Japanese Application No. 2023-502502, dated Sep. 3, 2024, with an English translation.

European Communication pursuant to Article 94(3) EPC for corresponding European Application No. 22 759 752.3, dated Dec. 15, 2025.

Japanese Office Action for corresponding Japanese Application No. 2023-502502, dated Feb. 18, 2025, with an English translation.

Enzo Life Sciences Inc., "Oxytocin ELISA kit", Product Manual, Catalog #: ADI-901-153A, Rev. Jan. 31, 2023. pp. 1-18 (20 pages total).

International Preliminary Report on Patentability and English translation of the Written Opinion of the International Searching Authority (PCT/IB/326, PCT/IB/373 and PCT/ISA/237) dated Sep. 7, 2023 for Application No. PCT/JP2022/007718.

International Search Report (PCT/ISA/210) dated Apr. 5, 2022 for Application No. PCT/JP2022/007718 with an English translation.

(Continued)

*Primary Examiner* — Jennifer Wecker

(74) *Attorney, Agent, or Firm* — Birch, Stewart, Kolasch & Birch, LLP

(57)                    ABSTRACT

An object of the present invention is to provide a simple purifying method, measuring method, and kit. The present invention is an oxytocin purifying method including treating a sample with an acid or a salt thereof, and treating the sample treated with the acid or the salt thereof with a hydrophobic carrier, and related to the purifying method, measuring method including the purifying method, and kit, in which the acid or the salt thereof is at least one or more acids or salts thereof selected from the group consisting of hydrochloric acid, acetic acid, sulfuric acid, sodium hydrogensulfate, potassium hydrogensulfate, lithium hydrogensulfate, ammonium sulfate, and a mixture thereof, and the hydrophobic carrier is a hydrophobic carrier having at least one or more functional groups on the surface, selected from the group consisting of an alkyl group having 4 to 6 carbon atoms, an alkylene glycol group, and a phenyl group.

7 Claims, No Drawings

Specification includes a Sequence Listing.

(56) References Cited

OTHER PUBLICATIONS

Schams, "Oxytocin determination by radioimmunoassay III. Improvement to subpicogram sensitivity and application to blood levels in cyclic cattle", Acta Endocrinologica, vol. 103, 1983, pp. 180-183.

Van De Heijning et al., "Solid-phase extraction of plasma vasopressin: evaluation, validation and application", Journal of Chromatography, vol. 565, 1991, pp. 159-171.

1

OXYTOCIN PURIFYING METHOD AND MEASURING METHOD AND KIT

BACKGROUND OF THE INVENTION

1. Field of the Invention

The present invention relates to an oxytocin purifying method, a measuring method, and a kit.

2. Description of the Related Art

Oxytocin is a peptide hormone composed of 9 amino acids, which is synthesized in the hypothalamus and secreted from the posterior lobe of the pituitary gland. As an assay of the oxytocin concentration in a biological specimen, an immunological measuring method, a high performance liquid chromatography method (HPLC), a liquid chromatography-mass spectrometry (LC/MS), or the like is commonly used. However, since the amount of oxytocin contained in the biological specimen is very small and a measurement interfering substance that is a protein such as albumin, a peptide, mucin, or the like contained in the biological specimen binds to oxytocin, it is difficult to accurately quantify oxytocin.

In the pretreatment method described in the commercialized ELISA kit for oxytocin (D. Schams, Oxytocin ELISA kit (Enzo Life Sciences Inc. USA) Catalog #: ADI-901-153A) and European Journal of Endocrinology, volume 103: Issue 2, 180-183, 1983, a biological specimen containing oxytocin is mixed with trifluoroacetic acid (TFA), a complex of oxytocin and a measurement interfering substance is adsorbed to a gel (C18 column), the measurement interfering substance is washed away from the gel with 0.1% TFA-H$_2$O, and then the oxytocin fraction is eluted with a mixed solution of 95% of acetonitrile and 5% of 0.1% TFA-H$_2$O. Furthermore, for preventing adverse effects of TFA on the measurement of oxytocin, it is necessary to perform a treatment of centrifugally concentrating the oxytocin fraction, further drying it at reduced pressure, and then reconstituting it with a measurement solvent. The TFA in the pretreatment method described in D. Schams, Oxytocin ELISA kit (Enzo Life Sciences Inc. USA) Catalog #: ADI-901-153A and European Journal of Endocrinology, volume 103: Issue 2, 180-183, 1983 is used as an ion pair reagent, and fractionation is performed using a C18 column in a state where a complex of oxytocin and a measurement interfering substance is formed.

SUMMARY OF THE INVENTION

The pretreatment method described in D. Schams, Oxytocin ELISA kit (Enzo Life Sciences Inc. USA) Catalog #: ADI-901-153A and European Journal of Endocrinology, volume 103: Issue 2, 180-183, 1983 has a large number of steps and is complicated for preventing an adverse effect of TFA on the measurement, and a long time is required for the pretreatment. Furthermore, it is difficult to perform the pretreatment method described in D. Schams, Oxytocin ELISA kit (Enzo Life Sciences Inc. USA) Catalog #: ADI-901-153A and European Journal of Endocrinology, volume 103: Issue 2, 180-183, 1983 in a hospital or the like that is not provided with a centrifuge. In view of the above-described circumstances, an object of the present invention is to provide a simple oxytocin purifying method.

[1] An oxytocin purifying method, the method including treating a sample with an acid or a salt thereof, and

2 treating the sample treated with the acid or the salt thereof with a hydrophobic carrier,
 in which the acid or the salt thereof is at least one or more acids or salts thereof selected from the group consisting of hydrochloric acid, acetic acid, sulfuric acid, sodium hydrogensulfate, potassium hydrogensulfate, lithium hydrogensulfate, ammonium sulfate, and a mixture thereof, and
 the hydrophobic carrier is a hydrophobic carrier having at least one or more functional groups on the surface, selected from the group consisting of an alkyl group having 4 to 6 carbon atoms, an alkylene glycol group, and a phenyl group.

[2] The method according to [1], in which the acid or the salt thereof is hydrochloric acid.

[3] The method according to [1] or [2], in which the hydrophobic carrier is a hydrophobic carrier having an alkyl group having 4 to 6 carbon atoms on the surface.

[4] The method according to [1], in which the acid or the salt thereof is hydrochloric acid, and the hydrophobic carrier is a hydrophobic carrier having an alkyl group having 4 to 6 carbon atoms on the surface.

[5] The method according to any one of [1] to [4], in which the sample is selected from the group consisting of a blood sample, urine, and saliva.

[6] A measuring method of oxytocin, including the oxytocin purifying method according to any one of [1] to [5].

[7] A kit for purifying oxytocin including at least one or more acids or salts thereof selected from the group consisting of hydrochloric acid, acetic acid, sulfuric acid, sodium hydrogensulfate, potassium hydrogensulfate, lithium hydrogensulfate, ammonium sulfate, and a mixture thereof, and a hydrophobic carrier having at least one or more functional groups on a surface selected from the group consisting of an alkyl group having 4 to 6 carbon atoms, an alkylene glycol group, and a phenyl group.

According to the present invention, oxytocin can be simply purified.

DESCRIPTION OF THE PREFERRED EMBODIMENTS

In the present specification, in a case where the upper limit and the lower limit of the range are indicated, it is indicated that A to B are equal to or more than A and equal to or less than B, unless otherwise specified. In addition, "measurement" in the present specification may include the meanings of quantitative, semi-quantitative, and qualitative. "Purification" in the present specification means bringing a sample into a state where the amount of oxytocin contained in a sample can be measured, and may include the meanings of isolation, recovery, extraction, concentration, and pretreatment.

<Oxytocin Purifying Method According to Embodiment of Present Invention>

The oxytocin purifying method according to the embodiment of the present invention (hereinafter, the purifying method according to the embodiment of the present invention) is a oxytocin purifying method including treating a sample with at least one or more acids or salts selected from the group consisting of hydrochloric acid, acetic acid, sulfuric acid, sodium hydrogensulfate, potassium hydrogensulfate, lithium hydrogensulfate, ammonium sulfate, or a mixture thereof (hereinafter, an acid treatment step), and treating the sample treated with the acid or salt using a hydrophobic carrier having at least one or more functional groups on a surface selected from the group consisting of an alkyl group having 4 to 6 carbon atoms, an alkylene glycol group, and a phenyl group (hereinafter, a hydrophobic carrier treatment step). According to the purifying method according to the embodiment of the present invention, oxytocin can be simply purified regardless of the equipment of the purification environment.

Oxytocin is a polypeptide consisting of 9 amino acids having the sequence of Cys-Tyr-Ile-Gln-Asn-Cys-Pro-Leu-Gly (SEQ ID NO: 1). The oxytocin in the present invention may be obtained from a biological specimen (natural oxytocin) or produced by a gene recombination method, or may contain a precursor of oxytocin. In addition, oxytocin may be a peptide into which a mutation has been introduced (mutant form), which is functionally equivalent to natural oxytocin. The mutation includes deletion or substitution of one or more amino acids, or addition of one or more amino acids. The amino acid sequence of the mutant form of oxytocin has at least 80% or more sequence identity with natural oxytocin, and may have 85% or more, 90% or more, or 95% or more sequence identity.

Examples of the sample according to the present invention include biological specimens obtained from a test animal, for example, blood samples such as serum, blood plasma, whole blood, and buffy coat, and body fluid samples such as cerebrospinal fluid, urine, saliva, semen, chest exudate, tears, sputum, mucus, lymph, ascites, pleural effusion, amniotic fluid, bladder lavage fluid, and bronchoalveolar lavage fluid, and the blood samples, the urine, and the saliva are preferable. In addition, the present invention is particularly useful for saliva because it contains abundant mucin which is a measurement interfering substance and binds to oxytocin. Examples of the test animal include mammals such as humans, monkeys, mice, rats, dogs, cats, pigs, rabbits, and chimpanzees, the humans, the monkeys, the mice, or the rats are preferable, and the humans are more preferable. The sample according to the present invention may be a sample derived from a culture medium (culture solution) in which cells or microorganisms are cultured, and examples thereof include a culture supernatant of the culture medium and an extract liquid obtained by lysing, disrupting, or the like the cells, in which oxytocin is recombinantly expressed using animal cells, plant cells, or bacterial cells as a host by a gene recombination method. Since the culture medium may contain an animal protein or the like to which oxytocin binds, such as albumin, the present invention is also useful for the culture medium. The sample according to the present invention may be directly used a sample collected from a test animal or a culture medium, or may be subjected to pretreatment such as recovery, concentration, dilution with a buffer solution or the like, and filtration sterilization. These pretreatments may be appropriately performed according to a conventional method.

The acid treatment step according to the present invention is a step of treating a sample with at least one or more acids or salts thereof (hereinafter, acid according to the present invention) selected from the group consisting of hydrochloric acid, acetic acid, sulfuric acid, sodium hydrogensulfate, potassium hydrogensulfate, potassium hydrogensulfate, lithium hydrogensulfate, ammonium sulfate, and a mixture thereof. Specifically, in the acid treatment step according to the present invention, by allowing the sample according to the present invention and the acid according to the present invention to coexist, for example, the pH of the solution after coexistence may be set to an acidic condition of less than 7, pH 1.5 to 6.0 is preferable, and pH 2.0 to 6.0 is more preferable. The amount of the acid according to the present invention to be allowed to coexist with the sample according to the present invention is, for example, 1 to 50 times (v/v), preferably 5 to 20 times (v/v), and more preferably 8 to 15 times (v/v) with respect to the sample containing oxytocin. As the acid according to the present invention, hydrochloric acid is preferable because oxytocin can be obtained with a high recovery rate regardless of the type of the sample. The acid according to the present invention may be used alone or in combination of two or more kinds. According to the acid treatment step according to the present invention, it is considered that oxytocin is separated from the complex formed by binding to a measurement interfering substance such as a protein or a peptide in the sample by treating the specimen with a specific acid.

The hydrophobic carrier treatment step according to the present invention is a step of treating the sample after the acid treatment step according to the present invention (hereinafter, acid-treated sample) using a hydrophobic carrier (hereinafter, hydrophobic carrier according to the present invention) having at least one or more selected functional groups on the surface, selected from the group consisting of an alkyl group having 4 to 6 carbon atoms, an alkylene glycol group, and a phenyl group. Specifically, the treatment is carried out by bringing the acid-treated sample into contact with the hydrophobic carrier according to the present invention, and separating oxytocin from other components in the acid-treated sample. The hydrophobic carrier treatment step according to the present invention is carried out by, for example, adding the acid-treated sample to the hydrophobic carrier (suspension) according to the present invention filled in a column or the like and performing elution; mixing or/and suspending the acid-treated sample with the hydrophobic carrier according to the present invention in a container, centrifuging as necessary, and then recovering the supernatant; or the like.

The alkyl group having 4 to 6 carbon atoms in the hydrophobic carrier according to the present invention may be linear, branched, or cyclic. Specific examples of such an alkyl group include a butyl group such as an n-butyl group, an isobutyl group, a sec-butyl group, a tert-butyl group, and a cyclobutyl group, a pentyl group such as an n-pentyl group, an isopentyl group, a sec-pentyl group, a tert-pentyl group, a neopentyl group, a 2-methylbutyl group, a 1,2-dimethylpropyl group, a 1-ethylpropyl group, and a cyclopentyl group, and a hexyl group such as an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, and a cyclohexyl group, and a linear or branched alkyl group having 4 to 6 carbon atoms is preferable, and the butyl group is more preferable.

Examples of the alkylene glycol group in the hydrophobic carrier according to the present invention include an oligoethylene glycol group, an oligopropylene glycol group, an oligo 1,3-propanediol group, an oligo 1,4-butanediol group, a polyethylene glycol group, a polypropylene glycol group, a poly 1,3-propanediol group, and a poly 1,4-butanediol group. Examples of the polyethylene glycol group, the polypropylene glycol group, the poly 1,3-propanediol group, and the poly 1,4-butanediol group include a group having, for example, 100 or more of repeating units thereof (alkylene glycol or alkanediol), and it may be a group having 100 to 500 of the repeating units. Examples of the oligoethylene glycol group, the oligopropylene glycol group, the oligo 1,3-propanediol group, and the oligo 1,4-butanediol group include a group having, for example, 2 to 99 of repeating units thereof (alkylene glycol or alkanediol), and it may be a group having 10 to 99 of the repeating units.

The hydrophobic carrier according to the present invention is a carrier having at least one or more functional groups on the surface of a solid phase (base material), selected from the group consisting of an alkyl group having 4 to 6 carbon atoms, an alkylene glycol group, and a phenyl group. The solid phase is not particularly limited as long as it is insoluble, and examples thereof include organic substances such as polystyrene, carboxylated polystyrene, polyacrylic acid, polymethacrylic acid, polymethyl methacrylate, poly-acrylamide, polyglycidyl methacrylate, polypropylene, polyolefin, polyimide, polyurethane, polyester, polyvinyl chloride, polyethylene, polychlorocarbonate, a silicone resin, a silicone rubber, agarose, dextran, an ethylene-maleic anhydride copolymer, and the like; inorganic substances such as glass, silicon oxides, diatom earth, porous glass, obscured glass, alumina, silica gel, metal oxides, and the like; cellulose derivatives; porous polymers; magnetic materials such as iron, cobalt, nickel, magnetite, chromite, and the like; and those prepared using an alloy of these magnetic materials as a material. Examples of the form of the solid phase include a gel (polymer gel), a microplate, a tube, a disk-like piece, particles (beads), and the like, and a gel (polymer gel) is preferable. The hydrophobic carrier according to the present invention may be used alone or in combination of two or more kinds. The hydrophobic carrier according to the present invention may be filled in a column or may be stored in a container such as a microtube.

Examples of commercially available hydrophobic carriers according to the present invention include TOYOPEARL™ Ether-650 (TOSOH CORPORATION, oligoethylene glycol group), TOYOPEARL™ PPG-600 (TOSOH CORPORATION, oligopropylene glycol group), TOYOPEARL™ Hexyl-650 (TOSOH CORPORATION, hexyl group), TOYOPEARL™ Butyl-650 (TOSOH CORPORATION, butyl group), TOYOPEARL™ Phenyl-650 (TOSOH CORPORATION, phenyl group), and the like.

The functional group provided on the surface of the hydrophobic carrier according to the present invention is preferably an alkyl group having 4 to 6 carbon atoms or an alkylene glycol group, and more preferably a linear or branched alkyl group having 4 to 6 carbon atoms, an oligoethylene glycol, a polyethylene glycol group, an oligopropylene glycol group, or a polypropylene glycol group, and still more preferably a butyl group. The functional group provided on the surface of the hydrophobic carrier according to the present invention may be used alone or in combination of two or more kinds.

The hydrophobic carrier treatment step according to the present invention may be performed in the presence of a salt, and is preferably performed in the presence of a salt. Examples of the salt include a sodium salt, a potassium salt, a magnesium salt, and an ammonium salt. The salt concentration in the case where the acid-treated sample is brought into contact with the hydrophobic carrier according to the present invention is, for example, 0.10 M to 5.0 M, and preferably 0.30 M to 1.0 M. By allowing the salt to coexist, the solution (supernatant or eluent) obtained by the hydrophobic carrier treatment step according to the present invention becomes neutral, and the measurement of oxytocin becomes easy. In addition, by adjusting the binding force of oxytocin and other components in the acid-treated sample to the hydrophobic carrier according to the present invention, separation of oxytocin and other components is facilitated. Specifically, the hydrophobic carrier treatment step according to the present invention is carried out by, for example, bringing the acid-treated sample into contact with a suspension containing the hydrophobic carrier according to the present invention and a salt in an amount where a final concentration is within the above-described range, bringing the hydrophobic carrier according to the present invention (as necessary, the suspension of the hydrophobic carrier according to the present invention) into contact with the acid-treated sample containing a salt in an amount where a final concentration is within the above-described range, or the like.

Specifically, the hydrophobic carrier treatment step according to the present invention is carried out by, for example, mixing or/and suspending the acid-treated sample with a suspension of a polymer gel having an alkyl group having 4 to 6 carbon atoms or an alkylene glycol group, which is the hydrophobic carrier according to the present invention, on the surface in a container (as necessary, at the presence of 0.30 M to 1.0 M of the salt), centrifuging as necessary, and then recovering the supernatant, or the like. In addition, the hydrophobic carrier treatment step according to the present invention is carried by, for example, adding the acid-treated sample to a suspension of a polymer gel having an alkyl group having 4 to 6 carbon atoms or an alkylene glycol group on the surface, which is the hydrophobic carrier according to the present invention filled in a column or the like (as necessary, at the presence of 0.30 M to 1.0 M of the salt), and recovering the solution eluted from the column.

<Measuring Method of Oxytocin>

The measuring method of oxytocin according to the embodiment of the present invention (hereinafter, the measuring method according to the embodiment of the present invention) is a method of measuring oxytocin using a sample subjected to the purifying method according to the embodiment of the present invention. Examples of the measuring method according to the embodiment of the present invention include a method commonly used for measuring a protein or a peptide such as an immunological assay, a high performance liquid chromatography method (HPLC), and a mass spectrometry method. Examples of the principles of these measuring methods include a sandwich method, a competition method, an aggregation method (immunonephelometry), an immunochromatography method, a Luminescent Oxygen Channeling Immunoassay (LOCI method), a capillary electrophoresis method such as a Liquid-phase Binding Assay-ElectroKinetic Analyte Transport Assay (LBA-EATA method) and a lectin electrophoresis method, a western blotting method, a surface plasmon resonance method (SPR method), and a lectin column method, and it may also be a homogeneous measurement system or a heterogeneous measurement system. According to the present invention, it is presumed that the anti-oxytocin antibody facilitates binding to oxytocin, and thus the immunological assay is more useful. The labeling in the immunological measuring method is not particularly limited, and examples of the immunological measuring method include an enzyme-linked immunosorbent assay (ELISA method), an enzyme immunoassay (EIA method), a radioimmunoassay (MA method), a fluorescent enzyme immunoassay (FETA method), a fluorescence immunoassay (FIA method), a chemiluminescent enzyme immunoassay (CLEIA method), a chemiluminescence immunoassay (CLIA method), and an electrochemiluminescence immunoassay (ECLIA method).

<Kit for Purifying Oxytocin According to Embodiment of Present Invention>

The kit for purifying oxytocin according to the embodiment of the present invention (hereinafter, the kit according to the embodiment of the present invention) includes (i) at least one or more acids or salts thereof (acids according to the present invention) selected from the group consisting of hydrochloric acid, acetic acid, sulfuric acid, sodium hydrogensulfate, potassium hydrogensulfate, lithium hydrogensulfate, ammonium sulfate, and a mixture thereof, and (ii) a hydrophobic carrier (a hydrophobic carrier according to the present invention) having at least one or more functional groups selected from the group consisting of an alkyl group having 4 to 6 carbon atoms, an alkylene glycol group, and a phenyl group. By using the kit according to the embodiment of the present invention in the method according to the embodiment of the present invention, oxytocin can be simply purified.

At least one or more acids or salts thereof selected from the group consisting of hydrochloric acid, acetic acid, sulfuric acid, sodium hydrogensulfate, potassium hydrogensulfate, lithium hydrogensulfate, ammonium sulfate, and a mixture thereof, and the hydrophobic carrier having at least one or more functional groups on the surface, selected from the group consisting of an alkyl group having 4 to 6 carbon atoms, an alkylene glycol group, and a phenyl group in the kit according to the embodiment of the present invention is the same as that in the oxytocin purifying method according to the embodiment of the present invention, and preferred ones and specific examples are also the same.

The acid according to the present invention in the kit according to the embodiment of the present invention may be a composition containing other components in addition to the acid. Examples of other components include preservatives (for example, sodium azide, salicylic acid, benzoic acid), reaction accelerators, excipients, and buffers. According to the present invention, in addition to the kit according to the embodiment of the present invention, there is also provided a kit for measuring oxytocin containing an optional component used for measuring oxytocin by various assays such as an immunological assay and a mass spectrometry method. Examples of the optional component include a sample diluent (a solution for diluting a sample), an antibody against oxytocin, a carrier, a labeling substance, a buffer solution, an enzyme solution, and a substrate solution. In addition, the kit according to the embodiment of the present invention may include an instruction manual or the like that describes the purifying method according to the embodiment of the present invention.

EXAMPLES

Hereinafter, the present invention will be specifically described based on Examples and Comparative Examples, but the present invention is not limited to these examples.

Example 1. Evaluation of Oxytocin Purifying Method (1) Acid Treatment

In a 1.5 mL PP vial, oxytocin (Anygen) was added to a urine specimen (FUJIFILM Wako Shibayagi Corporation) at a known concentration (within a range of 4.0 to 1000 pg/mL). To 200 µL of each of the obtained oxytocin-containing urine specimen and the oxytocin-free urine specimen, 20 µL of 1M hydrochloric acid at room temperature was added and stirred, and then the mixture was allowed to stand for 10 minutes to prepare an acid-treated sample.

(2) Hydrophobic Carrier Treatment

Then, 110 µL of the gel suspension [50% (w/v) TOYO-PEARL™ Butyl-650M (TOSOH CORPORATION), phosphate buffer solution (0.1 M phosphate buffer solution, 1.5 M NaCl)] was added to each of 220 µL of the acid-treated sample, stirred, and then allowed to stand for 10 minutes. The gel was stirred and then subjected to centrifugation (5000 g, 10 minutes, 4° C.), and the supernatant was used as a specimen for measurement.

(3) Measurement by ELISA Method

Anti Rabbit IgG Goat IgG (FUJIFILM Wako Shibayagi Corporation) purified by Protein G (cytiva) chromatography was immobilized on a 96-well microplate (Thermo Fisher Scientific, Inc.), and 100 µL/well of an anti-oxytocin rabbit polyclonal antibody (AIRPLANTS BIO) solution was added and allowed to stand at room temperature for 2 hours. After removing the antibody solution and washing, 50 µL/well of an oxytocin standard solution {an oxytocin standard solution prepared by using the Tris-HCl buffer solution [0.1 M Tris-HCl (FUJIFILM Wako Pure Chemical Corporation), 0.15 M NaCl (FUJIFILM Wako Pure Chemical Corporation), 0.1% BSA (Merck KGaA), 0.01% Tween20 (FUJIFILM Wako Pure Chemical Corporation), 1 mg/mL EDTA (DOJINDO Laboratories)] such that the amount of oxytocin was in the range of 4.0 to 1000 pg/mL} or 50 µL/well of the specimen for measurement, and 50 µL/well of a 10 pg/mL biotin-labeled oxytocin solution [a solution in which oxytocin (Anygen) bound to biotin (DOJINDO Laboratories) was dissolved in the Tris-HCl buffer solution] were each added thereto, stirred, and allowed to stand at room temperature for 2 hours. The reaction solution was removed and washed, and subsequently 100 µL/well of Avidin-HRP (Thermo Fisher Scientific, Inc.) prepared by using the Tris-HCl buffer solution was added thereto and allowed to stand at room temperature for 30 minutes. The reaction solution was removed and washed, then 100 µL/well of luminescent reagents (ELISA-Star Chemiluminescent Peroxidase Substrate, FUJIFILM Wako Pure Chemical Corporation) were each added thereto, and each of the luminescence intensity was measured using Infinite M200 PRO (Tecan Group Ltd.) by endpoint assay. A calibration curve was created from the measured values of the oxytocin standard solution by the ELISA method, and the oxytocin concentration was calculated based on the luminescence intensity of each specimen. The recovery rate (%) was calculated by multiplying by 100 the value obtained by dividing the oxytocin concentration calculated using the calibration curve from the value obtained from the measured value of "a urine specimen to which oxytocin having a known concentration was added" by subtracting "the measured value of the same urine specimen to which oxytocin was not added", by the oxytocin concentration (an added value of oxytocin having a known concentration) in the "the urine specimen to which oxytocin having a known concentration was added". The obtained recovery rates are shown in Table 1 below.

TABLE 1

| | Acid treatment | | Hydrophobic carrier treatment | | Recovery |
| --- | --- | --- | --- | --- | --- |
| | Acid | Concentration | Carrier | Specimen | rate (%) |
| Example 1 | Hydrochloric acid | 1M | Butyl-650M | Serum specimen | 91.4 |
| Example 2 | Hydrochloric acid | 0.25M | | | 99.4 |
| Example 3 | Acetic acid | 1M | | | 102 |
| Example 4 | Acetic acid | 0.25M | | | 79.1 |
| Example 5 | Sulfuric acid | 0.25M | | | 90.3 |
| Example 6 | Hydrochloric acid | 1M | | Urine specimen | 96 |
| Example 7 | Hydrochloric acid | 1M | | Saliva specimen | 93.2 |
| Example 8 | Hydrochloric acid | 1M | Ether-650M | Serum specimen | 107 |
| Example 9 | | | Phenyl-650M | | 109 |
| Example 10 | | | Hexyl-650C | | 97.1 |
| Example 11 | | | Ether-650M | Urine specimen | 86.5 |
| Example 12 | | | Phenyl-650M | | 79.5 |
| Example 13 | | | Butyl-650M | | 96 |
| Example 14 | | | Hexyl-650C | | 86.1 |
| Example 15 | | | Butyl-650M | Saliva specimen | 93.2 |
| Comparative Example 1 | — | | — | Serum specimen | Abnormally high value |
| Comparative Example 2 | Hydrochloric acid | 1M | — | | Abnormally high value |
| Comparative Example 3 | — | | Butyl-650M | | Abnormally high value |
| Comparative Example 4 | Hydrochloric acid | 1M | C8 | | Abnormally high value |
| Comparative Example 5 | Hydrochloric acid | 1M | C8 | | Abnormally high value |

Examples 2 to 15. Evaluation of Oxytocin Purifying Method

Oxytocin was purified, and then the measurement by the ELISA was performed method to calculate the recovery rate by the same method as in Example 1 except that the conditions described in Table 1 were adopted.

The reagents in Table 1 are as follows.

TOYOPEARL™ Ether-650M (TOSOH CORPORATION)

TOYOPEARL™ Phenyl-650M (TOSOH CORPORATION)

TOYOPEARL™ Hexyl-650C (TOSOH CORPORATION)

Serum specimen (BioIVT), saliva specimen (FUJIFILM Wako Shibayagi Corporation)

Table 1 shows the obtained recovery rates.

Comparative Example 1 to 5. Evaluation of Oxytocin Purifying Method

Measurement by the ELISA method was performed and the recovery rate was calculated by the same method as in Example 1 (3) except that the serum specimen itself was used as the measurement specimen without performing purification of oxytocin (acid treatment and hydrophobic carrier treatment) (Comparative Example 1). In addition, oxytocin was purified, and then the measurement by the ELISA was performed method to calculate the recovery rate by the same method as in Example 1 except that the conditions described in Table 1 were adopted (Comparative Examples 2 to 5). In the table, "-" indicates that the corresponding treatment has been not performed.

The reagents in Table 1 are as follows.

Sep-Pak C8 (Waters Corporation)

Table 1 shows the obtained recovery rates.

From Table 1, in a case where the measurement of oxytocin was performed without performing purification, an abnormally high value was obtained and the measurement was impossible. In addition, in the case of only the acid treatment with hydrochloric acid, the case of only the treatment with the hydrophobic carrier having a butyl group on the surface, or the purification in the case of combining the acid treatment with hydrochloric acid and the hydrophobic carrier treatment with C8, an abnormally high value was obtained and measurement was impossible. On the other hand, by purification combined with acid treatment with hydrochloric acid, sulfuric acid, or acetic acid and treatment with the hydrophobic carrier having a butyl group, a hexyl group, or an oligoethylene glycol group on the surface, oxytocin can be purified with a high recovery rate and measurement can be performed with high accuracy. In particular, it was found that a case where acid treatment with hydrochloric acid and treatment with the hydrophobic carrier having a butyl group on the surface are combined is particularly useful, since oxytocin can be purified with a high recovery rate even in a case where a serum specimen, a urine specimen, or a saliva specimen is used as a sample.

The oxytocin purifying method, the measuring method, and the kit for purification according to the aspect of the present invention, are useful in the field of measuring oxytocin, particularly in the field of clinical examination, because oxytocin can be simply purified. [Sequence table] 2211_ST250002.txt

What is claimed is:

1. A method that is an oxytocin purifying method, the method comprising:

treating a sample with an acid or a salt thereof; and treating the sample treated with the acid or the salt thereof with a hydrophobic carrier, by mixing or suspending the acid-treated sample with a suspension of the hydrophobic carrier in the presence of 0.3 M to 1.0 M of the salt, and centrifuging as necessary, such that a supernatant is recovered;

wherein the acid or the salt thereof is at least one or more acids or salts thereof selected from the group consisting of hydrochloric acid, acetic acid, sulfuric acid, sodium hydrogensulfate, potassium hydrogensulfate, lithium hydrogensulfate, ammonium sulfate, and a mixture thereof, and the hydrophobic carrier is a hydrophobic carrier having at least one or more functional groups on the surface, selected from the group consisting of an alkyl group having 4 to 6 carbon atoms, an alkylene glycol group, and a phenyl group.

2. The method according to claim 1, wherein the acid or the salt thereof is hydrochloric acid.

3. The method according to claim 1, wherein the hydrophobic carrier is a hydrophobic carrier having an alkyl group having 4 to 6 carbon atoms on the surface.

4. The method according to claim 1, wherein the acid or the salt thereof is hydrochloric acid, and the hydrophobic carrier is a hydrophobic carrier having an alkyl group having 4 to 6 carbon atoms on the surface.

5. The method according to claim 1, wherein the sample is selected from the group consisting of a blood sample, urine, and saliva.

6. A method of measuring oxytocin, comprising:

the oxytocin purifying method according to claim 1.

7. A kit for purifying oxytocin according to the method of claim 1, comprising:

at least one or more acids or salts thereof selected from the group consisting of hydrochloric acid, acetic acid, sulfuric acid, sodium hydrogensulfate, potassium hydrogensulfate, lithium hydrogensulfate, ammonium sulfate, and a mixture thereof; and a hydrophobic carrier having at least one or more functional groups on a surface, selected from the group consisting of an alkyl group having 4 to 6 carbon atoms, an alkylene glycol group, and a phenyl group.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Cys Tyr Ile Gln Asn Cys Pro Leu Gly
1               5
```